United States Patent [19]

Fish

[11] 4,061,015
[45] Dec. 6, 1977

[54] PIPE PRESSURE TESTING DEVICE

[75] Inventor: Frank L. Fish, Wichita, Kans.

[73] Assignee: Weaver Engineering & Mfg. Co., Wichita, Kans.

[21] Appl. No.: 702,743

[22] Filed: July 6, 1976

[51] Int. Cl.² .................................................. G01M 3/04
[52] U.S. Cl. .................................................. 73/49.5
[58] Field of Search .......................... 73/49.5, 49.1, 37

[56] References Cited

U.S. PATENT DOCUMENTS

| 2,396,380 | 3/1946 | Longley | 73/49.5 |
| 3,731,525 | 5/1973 | Suter | 73/49.5 |

FOREIGN PATENT DOCUMENTS

| 1,220,171 | 3/1964 | Germany | 73/49.1 |
| 2,308,123 | 2/1973 | Germany | 73/49.5 |
| 116,565 | 4/1969 | Norway | 73/49.5 |
| 245,418 | 6/1969 | U.S.S.R. | 73/49.1 |

Primary Examiner—Richard C. Queisser
Assistant Examiner—Joseph W. Roskos
Attorney, Agent, or Firm—Edwin H. Crabtree; John H. Widdowson

[57] ABSTRACT

A pipe pressure testing device for testing the strength of a pipe specimen hydrostatically. The device receiving fluid under pressure and applying the fluid against the inner circumference of the pipe specimen and along the length thereof.

6 Claims, 4 Drawing Figures

PIPE PRESSURE TESTING DEVICE

BACKGROUND OF THE INVENTION

This invention relates generally to pressure testing devices and more particularly, but not by way of limitation, to a pipe pressure testing device for testing the strength of a pipe hydrostatically.

Heretofore, the strength of a pipe has been tested hydrostatically by attaching end caps to a pipe specimen and applying fluid under pressure inside the pipe specimen until the specimen ruptures. This type of testing applies end pressure to approximately the entire area of the end caps making it difficult to secure the end caps to the specimen at high pressures. Also, it is required to fill all of the interior of the pipe specimen with the fluid and not until the specimen is filled will the pressure of the fluid be brought up to the pressure required to test the strength of the pipe.

Also, there are prior art testing devices which have used center tubes inserted through the pipe specimen to reduce the area required to fill with fluid pressure. The center tube is attached to end caps which are secured to each other by connecting rods, bolts, and screws. These types of testing devices are cumbersome and time consuming in attaching to the pipe specimen and dismantling. Also, the devices are heavy and difficult to handle by hand.

The pipe pressure testing device as disclosed herein greatly reduces the above-described problems and efficiently and accurately tests the strength of the pipe.

SUMMARY OF THE INVENTION

The subject invention is a lightweight, hand assembled pipe pressure testing device for the testing of a pipe specimen such as an irrigation pipe, municipal water pipe, and various other types of pipes made of plastic, cast iron, aluminum, steel, or the like.

The invention is easy to assemble and eliminates the use of bolts, nuts, and retaining rods for connecting together the end caps attached to the ends of the pipe specimen.

The invention includes a center tube disposed inside the inner circumference of the pipe specimen thereby reducing the area of the end caps exposed to high pressure during the testing of the pipe specimen. By having a center tube inside the test specimen the amount of fluid required in testing the pipe specimen is greatly reduced and the pressure required in testing the specimen can be obtained rapidly.

Also, various diameters of pipe specimens can be tested using the same pipe pressure testing device by merely interchanging end caps having the same diameter as the specimen.

The pipe pressure testing device can be used on various size diameters of pipes ranging up to a 15 inch diameter or greater, as the case may be. The testing device is designed for testing a pipe specimen up to 1,000 p.s.i. with a 100% safety factor.

The pipe pressure testing device includes an elongated center tube having a smaller diameter and a greater length than the pipe specimen. The center tube is inserted inside the pipe specimen with the ends of the center tube extending outwardly from both ends of the specimen. A pair of hollow end caps are received around the outer circumference of the ends of the center tube. A portion of the caps is received around the outer circumference of the pipe specimen and attached to the ends thereof. One of the caps includes a conduit therethrough communicating with the outside of the cap and the space between the outer circumference of the center tube and the inner circumference of the pipe specimen. The conduit receives the prssurized fluid therethrough. The hollow end caps are secured to the ends of the center tube and the pipe specimen by hollow restraining collars received around the outer circumference of the center tube. The hollow restraining collars have apertures therethrough for inserting restraining pins therein and through apertures in the ends of the center tube.

The advantages and objects of the invention will become evident from the following detailed description when read in conjunction with the accompanying drawings which illustrate the preferred embodiments of the invention.

DETAILED DESCRIPTION OF THE DRAWINGS

Figure 1:
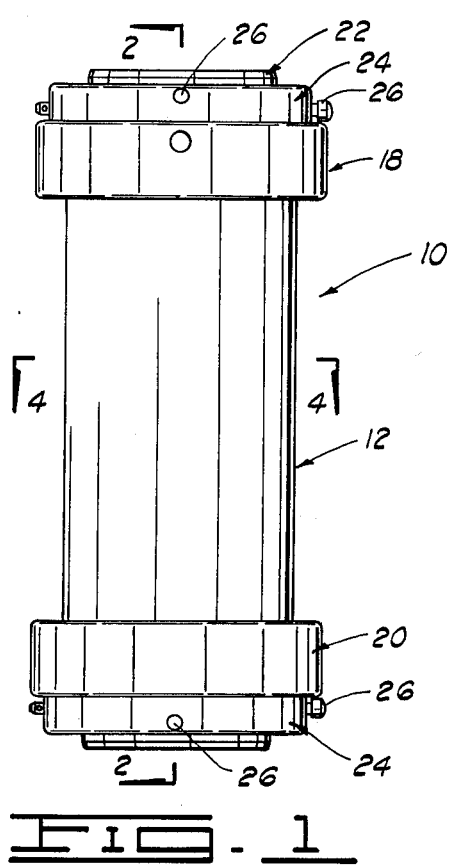
FIG. 1 is a side view of the pipe pressure testing device.

In FIG. 1, the pipe pressure testing device is designated by general reference numeral 10. The testing device 10 is attached to a pipe specimen 12. The pipe specimen 12 includes an outer circumference 14 and an inner circumference 16 shown in FIGS. 2 and 4.

The testing device 10 includes a first end cap 18, a second end cap 20, a center tube 22, restraining collars 24 and restraining pins 26 inserted through apertures in the restraining collars 24 and center tube 22 for securing the end caps 18 and 20 to the test specimen 12.

Figure 2:
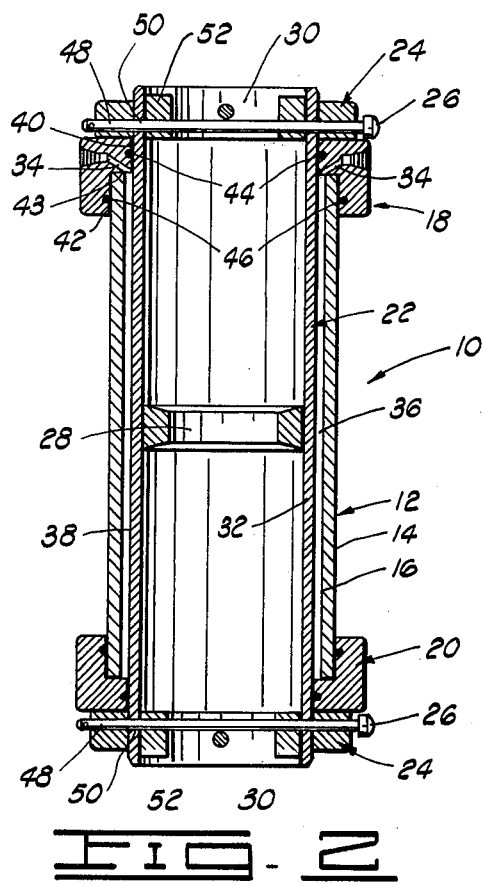
FIG. 2 is a sectional side view of the pipe pressure testing device taken along lines 2—2 shown in FIG. 1.

In FIG. 2, a side sectional view of the testing device 10 taken along lines 2—2 shown in FIG. 1 is illustrated. In this view, a center reinforcing ring 28 and end reinforcing rings 30 are disposed inside an inner circumference 32 of the center tube 22. The center reinforcing ring 28 and the end reinforcing rings 30 provide support for the center tube 22 during the testing of the pipe specimen 12.

In the first end cap 18 a conduit 34 is bored therethrough from the outside of the cap 18 into an area 36 between the inner circumference 16 of the pipe specimen 12 and an outer circumference 38 of the center tube 22. By applying a pressurized fluid through the conduit 34 into the area 36 between the inner circumference 16 of the pipe specimen 12 and the outer circumference 38 of the center tube, the strength of the specimen 12 is tested hydrostatically.

In this cross sectional view, the first end cap 18 and second end cap 20 can be seen having a first inner circumference 40 and a second inner circumference 42 with a flange portion 43 therebetween. The first inner circumference 40 is disposed around the outer circumference 38 of the center tube 22. The second inner circumference 42 is disposed around the outer circumference 14 of the pipe specimen 12. The flange portion 43 is disposed against the ends of the pipe specimen 12 and provides a seal at both ends of the area 36. The first inner circumference 40 and the second inner circumference 42 of the end caps 18 and 20 further include "O"-rings 44 and 46 therearound to prevent leakage of the pressurized fluid during the testing of the pipe specimen 12.

The end caps 18 and 20 are held in place against the pipe specimen 12 by inserting the restraining pins 26 through apertures 48 in the restraining collars 24, apertures 50 in the ends of the center tube 22, and apertures 52 in the reinforcing rings 30.

Figure 3:
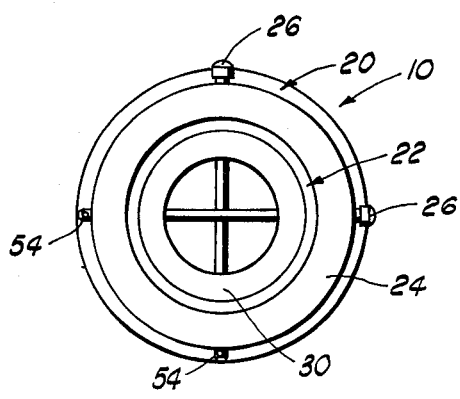
FIG. 3 is an end view of the pipe pressure testing device.

In FIG. 3, an end view of the testing device 10 is illustrated. In this view, the end of the hollow center tube 22 can be seen extending through the restraining collar 24 with the restraining collar 24 disposed adjacent the end cap 20. Also seen are restraining pins 26 extending through the restraining collar 24, center tube 22, and reinforcing rings 30. The ends of the pins 26 include spring loaded keepers 54 to hold the pins 26 in place.

Figure 4:
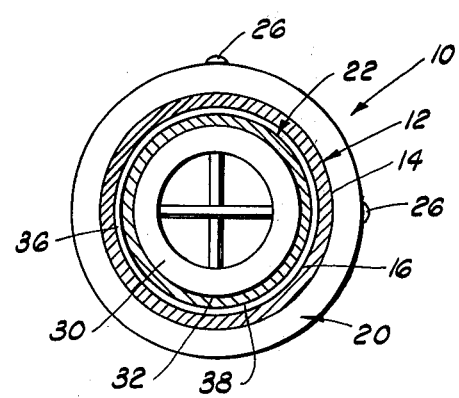
FIG. 4 is a sectional end view of the pipe pressure testing device taken aong lines 4—4 shown in FIG. 1.

In FIG. 4 a sectional end view taken along lines 4—4 shown in FIG. 1 is illustrated. In this view, the center tube 22 can be seen disposed inside the inner circumference 16 of the pipe specimen 12 with the area 36 therebetween for receiving the pressurized fluid therein.

In operation, the pipe specimen 12 to be tested is cut having a length shorter than the length of the center tube 22. Also, the pipe specimen 12 will have an inner diameter greater than the outer diameter of the center tube 22. The center tube 22 is inserted inside the pipe specimen 12 with the ends of the center tube 22 extending outwardly from both ends of the pipe specimen 12. A first end cap 18 and second end cap 20 are selected having a second inner circumference 42 the same as the circumference 14 of the pipe specimen 12. The end caps 18 and 20 are inserted around the ends of the test specimen 12 and the end of the center tube 22. The end caps 18 and 20 are held in place by inserting the restraining collars 24 around the remaining end of the center tube 22 and inserting the restraining pins 26 through the apertures 48, 50, and 52. The test specimen is now ready for testing and the pressurized fluid is applied through the conduit 34 into the area 36 between the inner circumference 16 of the pipe specimen 12 and the outer circumference 38 of the center tube 22.

When the test has been completed, the pressurized fluid is drawn from the test device 10 and the restraining pins 26 are removed. The restraining collars 24 and the first end cap 18 and second end cap 20 are then removed from the pipe specimen 12 and the center tube 22. The center tube 22 is then removed from inside the pipe specimen 12.

Changes may be made in the construction or arrangement of the parts or elements of the embodiments as disclosed herein without departing from the spirit or scope of the invention as defined in the following claims.

I claim:

1. A pipe pressure testing device for testing the strength of an elongated pipe specimen hydrostatically, the device comprising:

an elongated center tube having a smaller diameter and greater length than the pipe specimen, said center tube inserted inside the pipe specimen, the ends of said center tube extending outwardly from both ends of the pipe specimen;

a pair of hollow end caps, said end caps having a first inner circumference and a second inner circumference with a flange portion therebetween, the first inner circumference received around the ends of said center tube with the ends of said center tube extending therethrough, the second inner circumference received around the ends of the pipe specimen, the flange portion providing a seal between the outer circumference of said center tube and the inner circumference of the pipe specimen, one of said caps including a conduit therethrough and communicating with the outside of the cap and the space between the outer circumference of said center tube and the inner circumference of the pipe specimen, said circuit receiving pressure fluid therethrough; and a pair of hollow restraining collars received around the outer circumference of the ends of said center tube and disposed adjacent the outside of said caps, and restraining pins inserted through apertures in said restraining collars and indexed with apertures in the ends of said center tube for securing said caps against the ends of the pipe specimen.

2. The testing device as described in claim 1, wherein said restraining pins include a pair of restraining pins at each end of said center tube, said pins disposed in the apertures at right angles to each other with the ends of said pins received in apertures on the opposite side of said collars and said tube.

3. The testing device as described in claim 1, further including a center reinforcing ring received in the inner circumference of said center tube and centered therein for supporting the inside of said center tube.

4. The testing device as described in claim 3, further including a pair of end reinforcing rings received in the inner circumference of said center tube and positioned at the ends of said center tube for supporting the inside of said center tube.

5. The pipe testing device as described in claim 4, wherein said end reinforcing rings include apertures therethrough for receiving said restraining pins when said restraining collars are secured against said end caps.

6. A pipe pressure testing device for testing the strength of an elongated pipe specimen hydrostatically, the device comprising:

an elongated center tube having a smaller diameter and greater length than the pipe specimen, said center tube insertd inside the pipe specimen, the ends of said center tube extending outwardly from both ends of the pipe specimen;

a pair of hollow end caps, said end caps having a first inner circumference and a second inner circumference with a flange portion therebetween, the first inner circumference received around the ends of said center tube with the ends of said center tube extending therethrough, the second inner circumference received around the ends of the pipe specimen, the flange portion providing a seal between the outer circumference of said center tube and the inner circumference of the pipe specimen, one of said caps including a conduit therethrough and communicating with the outside of the cap and the space between the outer circumference of said center tube and the inner circumference of the pipe specimen, said conduit receiving pressure fluid therethrough;

a center reinforcing ring received in the inner circumference of said center tube and centered therein for supporting the inside of said center tube;

a pair of end reinforcing rings received in the inner circumference of said center tube and positioned at the ends of said center tube for supporting the inside of said center tube, said end reinforcing rings including apertures therethrough; and a pair of hollow restraining collars received around the outer circumference of the ends of said center tube and disposed adjacent the outside of said caps, and a pair of restraining pins at each end of said center tube, said pins inserted through apertures in said restraining collars and indexed with apertures in the ends of said center tube and the apertures in said end reinforcing rings, the ends of said pins received in apertures on the opposite side of said collars, said tube, and said end reinforcing rings, said pins disposed at right angles to each other.

* * * * *

UNITED STATES PATENT AND TRADEMARK OFFICE
CERTIFICATE OF CORRECTION

PATENT NO. : 4,061,015
DATED : December 6, 1977
INVENTOR(S) : Frank L. Fish

It is certified that error appears in the above-identified patent and that said Letters Patent are hereby corrected as shown below:

IN THE SPECIFICATIONS

Column 2, line 5, correct the spelling of the word "pressurized".

Column 2, line 27, correct the spelling of the word "along".

IN THE CLAIMS

Claim 1, column 4, line 11, after the word "said", delete "circuit" and add --- conduit ---.

Signed and Sealed this

Fourth Day of April 1978

[SEAL]

Attest:

RUTH C. MASON
Attesting Officer

LUTRELLE F. PARKER
Acting Commissioner of Patents and Trademarks